(12) United States Patent
Harrison

(10) Patent No.: US 6,216,040 B1
(45) Date of Patent: Apr. 10, 2001

(54) IMPLANTABLE MICROPHONE SYSTEM FOR USE WITH COCHLEAR IMPLANTABLE HEARING AIDS

(75) Inventor: William Vanbrooks Harrison, Valencia, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/375,462

(22) Filed: Aug. 17, 1999

Related U.S. Application Data

(60) Provisional application No. 60/098,597, filed on Aug. 31, 1998.

(51) Int. Cl.$^7$ ........................................... A61N 1/34
(52) U.S. Cl. .................................................. 607/57
(58) Field of Search ................................. 607/55, 56, 57, 607/137; 600/25

(56) References Cited

U.S. PATENT DOCUMENTS

| 4,267,410 | 5/1981 | Forster et al. | 179/107 |
| 4,428,377 | 1/1984 | Zollner et al. | 128/419 |
| 4,532,930 | 8/1985 | Crosby et al. | 128/419 |
| 5,603,726 | 2/1997 | Schulman et al. | 607/57 |
| 5,730,699 | 3/1998 | Adams et al. | 600/25 |
| 5,814,095 | 9/1998 | Muller et al. | 607/57 |

FOREIGN PATENT DOCUMENTS 9718689   5/1997   (WO) .

*Primary Examiner*—Scott M. Getzow
(74) *Attorney, Agent, or Firm*—Bryant R. Gold

(57) ABSTRACT

An implantable microphone system senses "sound" by sensing motion of middle ear components without having to physically touch or contact such elements. In one embodiment, acoustically induced vibrations in any of the moving components of the middle ear are detected using a pulsed echo Doppler ultrasound transducer, implanted in the middle ear. The implantable microphone system is ideally suited for use with a cochlea implant device.

18 Claims, 5 Drawing Sheets

IMPLANTABLE MICROPHONE SYSTEM FOR USE WITH COCHLEAR IMPLANTABLE HEARING AIDS

This application claims the benefit of U.S. patent application Ser. No. 60/098,597, filed Aug. 31, 1998.

BACKGROUND OF THE INVENTION

The present invention relates to an implantable microphone system that is useable with cochlear implants or implantable hearing aids, and more particularly to an implantable microphone system that senses motion of middle ear components without physically touching such elements.

A cochlear implant is an electronic device designed to provide useful hearing and improved communication ability to individuals who are profoundly hearing impaired and unable to achieve speech understanding with hearing aids. Hearing aids (and other types of assistive listening devices) make sounds louder and deliver the amplified sounds to the ear. For individuals with a profound hearing loss, even the most powerful hearing aids may provide little to no benefit.

A profoundly deaf ear is typically one in which the sensory receptors of the inner ear, called hair cells, are damaged or diminished. Making sounds louder or increasing the level of amplification, e.g., through the use of a hearing aid, does not enable such an ear to process sound. In contrast, cochlear implants bypass damaged hair cells and directly stimulate the hearing nerves with electrical current, allowing individuals who are profoundly or totally deaf to receive sound.

In order to better understand how a cochlear implant works, and how the present invention is able to function, it is helpful to have a basic understanding of how the ear normally processes sound. The ear is a remarkable mechanism that consists of three main parts: the outer ear, the middle ear and the inner ear. The outer ear comprises the visible outer portion of the ear and the ear canal. The middle ear includes the eardrum and three tiny bones. The inner ear comprises the fluid-filled snail-shaped cochlea with contains thousands of tiny hair cells.

When the ear is functioning normally, sound waves travel through the air to the outer ear, which collects the sound and directs it through the ear canal to the middle ear. The sound waves strike the eardrum (tympanic membrane) and cause it to vibrate. This vibration creates a chain reaction in the three tiny bones in the middle ear. These three tiny bones are medically termed the malleus, incus and stapes, but are also commonly referred to as the "hammer", "anvil" and "stirrup". Motion of these bones, in turn, generates movement of the oval window, which in turn causes movement of the fluid contained in the cochlea.

As indicated above, the cochlea is lined with thousands of tiny sensory receptors commonly referred to as hair cells. As the fluid in the cochlea begins to move, the hair cells convert these mechanical vibrations into electrical impulses and send these signals to the hearing nerves. The electrical energy generated in the hearing nerves is sent to the brain and interpreted as "sound".

In individuals with a profound hearing loss, the hair cells are damaged or depleted. In these cases, electrical impulses cannot be generated normally. Without these electrical impulses, the hearing nerves cannot carry messages to the brain, and even the loudest of sounds may not be heard.

Although the hair cells in the cochlea may be damaged, there are usually some surviving hearing nerve fibers. A cochlear implant works by bypassing the damaged hair cells and stimulating the surviving hearing nerve fibers with an electrical signal. The stimulated nerve fibers then carry the electrical signals to the brain, where they are interpreted as sound.

Representative cochlear implant devices are described in U.S. Pat. Nos. 4,267,410; 4,428,377; 4,532,930; and 5,603,726, incorporated herein by reference.

Cochlear implants currently use external microphones placed on the body that pick up sound (sense acoustic pressure waves and convert them to electrical signals) and then transmit the electrical signals to a signal processor for amplification, processing and conversion into an electrical stimulation signal (either current or voltage) that is applied to the surviving acoustic nerves located in the cochlea. Such a microphone is, by design, very sensitive, and in order to be sensitive, is by its nature very fragile. Disadvantageously, the external microphone can be damaged if it becomes wet, is dropped or is exposed to extreme conditions frequently encountered in the external environments. These fragile and sensitive microphones also restrict the user's lifestyle and activities. For example, when a user must wear a microphone, he or she is restricted from participation in swimming and other sports, e.g., contact sports, unless the microphone is removed during such activities. If the microphone is removed, however, the user no longer is able to hear. Moreover, many users also find external microphone cosmetically objectionable since they appear out of place and mark the user as "needing assistance".

It thus evident that improvements are needed in the way users of a cochlear implant, or other hearing aid systems, sense or hear sounds, and more particularly, it is evident that improvements are needed in the microphones used with such systems.

SUMMARY OF THE INVENTION

The present invention addresses the above and other needs by replacing the external microphone commonly used with cochlear implants and other hearing aid systems with an implantable microphone system. Advantageously, such implantable microphone system hears "sound" by sensing motion of middle ear components without having to physically touch such elements.

In broad terms, the invention may be summarized as an implantable microphone system that includes: (1) a sensor for sensing motion of middle ear components without physical contact with middle ear components, wherein the sensor is at least partially implantable within the middle ear; and (2) processing means coupled to the sensor for converting the sensed motion to an electrical output signal. Advantageously, the electrical output signal thus functions as a microphone output signal that varies as a function of acoustic sound waves received through the outer ear and impressed upon the movable middle ear components.

In accordance with one aspect of the invention, the surviving tympanic membrane or other middle ear components is/are used as the diaphragm for a fully implanted microphone. Even though hearing may be lost, most individuals who are characterized as profoundly deaf still have a fully functioning tympanic membrane and middle ear components. The present invention advantageously relies on the response of such fully functioning tympanic membrane or other middle ear components as incoming acoustic pressure waves are received in the outer ear and funneled into the ear canal. The acoustically induced vibrations in any of these moving components in the middle ear are detected using, in one preferred embodiment, a pulsed echo Doppler ultrasound transducer, implanted in the middle ear, and electronic processing means. Other embodiments of the invention may detect the moving components in the middle ear using an optical sensor, or the like.

In operation, the acoustic Doppler transducer exposes a moving component of the middle ear with an ultrasonic signal and receives acoustic reflections from the target anatomy. If the target is moving the received signal will be shifted up or down in frequency by an amount that is proportional to the velocity and displacement of the target movement and the mean velocity of the media filling the separation space between the transducer and the target. This frequency is given by the Doppler equation.

In other embodiments of the invention, an appropriate transducer, e.g., an optical, microwave, infrared, or RF transceiver, similarly exposes one or more moving components of the middle ear with an optical or other electromagnetic signal and receives signal reflections from the target anatomy. When the target anatomy is moving, such movement is detectable in the energy content of the reflected signal.

Thus, it is seen that the implantable microphone system provided by the invention is directed broadly to systems and methods for detecting motion of the functioning middle ear components without having to physically be in contact with such moving middle ear components. One embodiment of the invention focuses on the use of a pulsed echo Doppler ultrasound transducer. It is to be understood, however, that the invention contemplates the use of other types of transducers that sense motion of the middle ear components without physical contact therewith, For example, as indicated, optical, infrared, and/or rf systems may be used that sense reflected variations in radiation directed to the moving components of the middle ear.

The present invention offers the advantage of an implantable microphone system that uses many of the acoustic properties of the ear that nature provided. That is, because both the outer ear and middle ear components are used, the directional performance for sensing sound is enhanced. Moreover, there may be, for some patients, a natural stapedius response provided by the natural tightening of the tympanic membrane by the stapedius tendon. Further, the location of the device in the middle ear also provides protection from the outside environment as well as a cosmetic enhancement.

The invention may also be characterized as a method of sensing sound using implantable components and generating a microphone signal representative of the sensed sound, which microphone signal is useable by a cochlear implant or other hearing aid device. The method comprises the steps of: (a) implanting a motion sensor in the middle ear, the motion sensor including means for sensing movement of at least one middle ear component without making physical contact with the at least one middle ear component; (b) sensing motion of at least one of the moveable middle ear components using the implanted motion sensor; and (c) converting the sensed motion of at least one middle ear component to the microphone signal representative of sensed sound. In one preferred embodiment, the motion sensor comprises a Doppler sensor configured to sense the Doppler frequency shift associated with an interrogating Doppler signal directed to at least one of the moving elements of the middle ear.

It is thus an object of the present invention to provide an implantable microphone that may be used with a cochlear implant or other hearing aid system.

It is a further object of the invention to provide an implantable microphone system that utilizes many of the natural acoustic properties of the ear that nature provided, such as the ability to use the outer ear to collect and direct sound into the ear canal, and the ability to use the functioning middle ear components without interference with the motion of such middle ear components through physical contact therewith.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
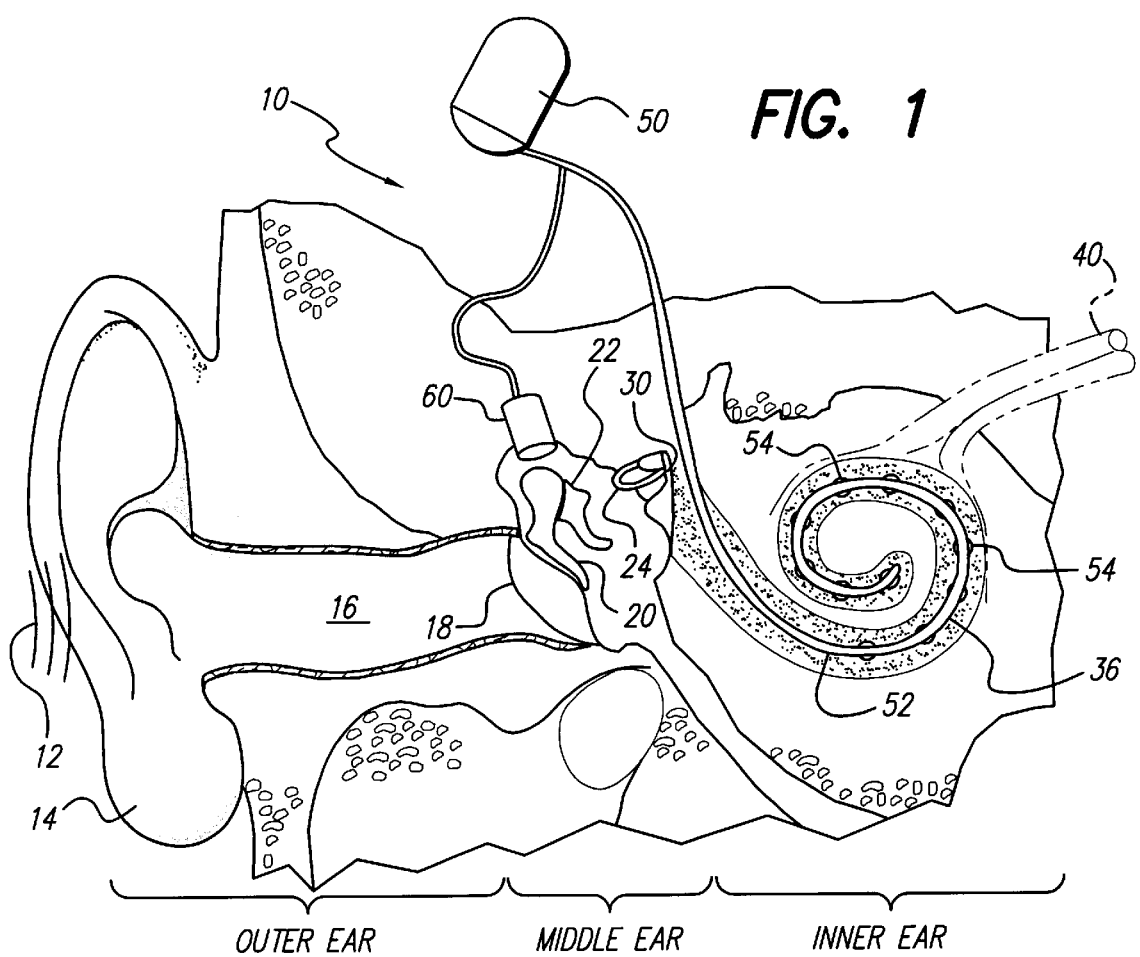
FIG. 1 is a functional schematic diagram of the ear, showing the manner in which an implantable microphone system is made through the use of a sensor implanted within the middle ear.

With reference to FIG. 1, there is shown a functional block diagram of an implantable microphone system 10 in accordance with the present invention. Also schematically shown in FIG. 1 are the major relevant components of the outer, middle and inner ear that typically play a role when using the invention.

The outer ear includes the auricle 14 and the ear canal 16. An acoustic pressure wave, represented in FIG. 1 by the short parallel lines 12, is collected by the auricle 14 and funneled into the ear canal 16. At the end of the ear cannel 16 is the "ear drum" 18, or in medical terms, the tympanic membrane 18. In a normal person (a person who is not significantly hearing impaired) the received acoustic wave 12 causes the tympanic membrane 18 to vibrate, which vibration is coupled through three tiny bones, the malleus ("hammer") 20, the incus ("anvil") 22 and the stapes ("stirrup") 24, to the oval window 30. These bones of the middle ear serve to filter and amplify the perceived acoustic wave 12, causing the oval window 30 to articulate, or vibrate, in response to the acoustic wave 12. Vibration of the oval window, in turn, sets up waves of fluid motion within the fluid contained within the snail-shaped cochlea 36. Such fluid motion, in turn, activates tiny hair cells (not shown in FIG. 1) that line the inside of the cochlea 36. Activation of the hair cells causes appropriate nerve impulses to be transferred through the spiral ganglion 40 to the brain, where they are perceived as sound.

For many individuals who suffer from profound deafness, the hair cells have been damaged to the point where it is not possible to activate them. Hence, an implantable cochlear stimulator (ICS) 50 may be implanted near the ear, and an electrode array 52, having a plurality of spaced apart electrodes 54 thereon, is inserted into the cochlea 36. As explained previously, such ICS 50, when used in conventional manner, e.g., as taught in the referenced patents, is coupled to an external microphone that senses sounds. Such coupling may occur through various means, but is usually achieved through an inductive coupling link with an external head piece, connected to a wearable processor. Such link also provides a way for power to be coupled into the implanted ICS 50. The sounds sensed by the external microphone are processed and converted to appropriate electrical stimuli that are selectively applied to the electrode contacts 54 of the electrode array 52. Such electrical stimuli bypass the defective hair cells and directly activate the nerves within the of the spiral ganglion, causing nerve impulses to be transferred to the brain, where they may be perceived as sound.

In contrast to the conventional method of using an ICS as explained in the previous paragraph, the present invention utilizes an implantable sensor 60 coupled to an implantable cochlear stimulator (ICS) 50, as shown in FIG. 1, as an implantable microphone system 10. As seen in FIG. 1, the sensor 60 is implanted so that at least a portion of it resides within the middle ear, but so that it does not physically come in contact with the moving elements that reside within the middle ear. That is, the sensor 60 does not physically come in contact with the tympanic membrane 18, the malleus 20, the incus 22, the stapes 24, or the oval window 30.

Figure 2:
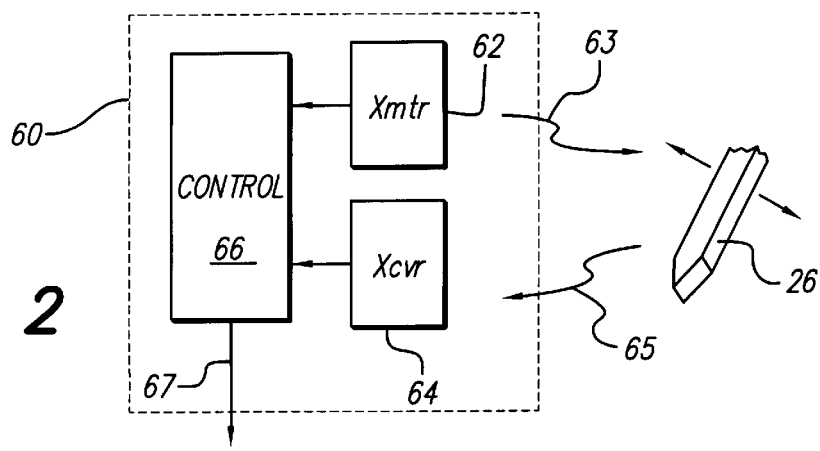
FIG. 2 is a simplified block diagram of the sensor of FIG. 1.

The sensor 60, as illustrated in FIG. 2, typically includes a transmitter portion 62 and a receiver portion 64, each of which is appropriately controlled by a control circuit 66. In operation, the transmitter portion 62 generates an appropriate interrogation signal, either on a continuous wave (CW) or pulsed basis. Such interrogation signal is represented in FIG. 2 by the wavy arrow 63 and is hereafter referred to as the interrogation signal 63. The interrogation signal 63 is directed or focused so that it irradiates at least one of the moving elements 26 within the middle ear, i.e., the tympanic membrane 18, the malleus 20, the incus 22, the stapes 24, or the oval window 30. A portion of the signal 63 is reflected from the moving element 26, and such reflected portion, represented in FIG. 2 as the wavy arrow 65 (and hereafter referred to as the reflected signal 65), is detected by the receiver portion 64 of the sensor 60.

The reflected signal 65 is modulated in accordance with the degree of movement associated with the movable element 26 within the middle ear. Thus, by appropriately demodulating the control signal 65, e.g., using demodulating circuits within the control circuit 66, an output signal 67 is generated representative of the sensed movement of the movable element 26, which movement, in turn, corresponds with the received acoustic pressure waves 12 (FIG. 1). That is, the output signal 67 comprises a signal representative of the sound that is received within the ear. In this manner, it is seen that the microphone system 10 uses at least one of the moving elements 26 of the middle ear as its diaphragm in order to convert acoustic pressure waves to an output signal, e.g., an electrical output signal.

While the transmitter portion 62 and the receiver portion 64 of the implantable sensor 60 are shown in FIG. 2 as separate elements, it is to be understood that for some applications the transmitting and receiving functions may be carried out by the same element.

One specific implementation of the invention involves the use of ultrasonic acoustic Doppler shift. In accordance with this implementation, an acoustic transducer is used as the sensor 60 to interrogate any of the moving elements in the middle ear to derive a Doppler shift signal. This signal is detected and converted into an electrical signal that is proportional to the audio energy present at the tympanic membrane. The transducer can be used to detect tympanic membrane vibrations without making physical contact to any moving element. This approach provides the significant benefit of preserving the natural hearing mechanics of the individual while not loading any of the moving system with additional masses that would alter its natural acoustic response.

There are several approaches that may be used in accordance with the present invention in order to implement the basic concept of the invention as described above. The feature common to all approaches or implementations of the invention is to use an active rather then a passive approach to produce an implantable microphone that uses the moving elements of the middle ear. In fact, almost any dynamic parameter that changes in response to acoustic pressure on the tympanic membrane may be used to produce an electrical signal that represents this pressure. These parameters can include physical motion, pressure variation in water, pressure variation in air, etc.

One approach used by the invention, as indicated above, is Doppler shift. The Doppler shift relies on the property that a signal traveling through a media with a constant velocity of propagation and encountering a moving target is shifted by an amount proportional to the ratio of the velocity of that target and the velocity of propagation. Using ultrasound (acoustic waves) has some advantages as well as disadvantages when sensing Doppler shift. The acoustic wavelengths are relatively long and this places a constraint on the lower limit of detectable positional displacement of the target (the moving element within the middle ear). The use of an active rather than passive means to measure acoustic pressure will cause a slight increase in power consumption. One advantage and benefit of this approach is that the normal ear mechanics are used to provide the hearing device. Also, since, this method makes no physical contact to the moving parts, the normal motion of the middle ear components is not impeded. Since ultrasonic waves can travel through fluid as well as air, although with different velocities, this significantly reduces the sensitivity of this method to fluid or tissue accumulation in the middle ear.

Other approaches used by the invention relate to the use of other types of signal emitters 62 (FIG. 2) that emit radiation 63 of a particular type, e.g., optical, infrared, RF, or other electromagnetic radiation. In accordance with these other approaches, a suitable receiver 64, compatible with receiving the type of radiation emitted, receives the radiation after such radiation has been affected by movement of at least one middle ear component 26. As used herein, "affected by" means the characteristics of the received signal, e.g., its amplitude, frequency, phase, energy content, morphology (shape), pulse width, or the like, are somehow influenced by the motion of one or more middle ear components 26. Further, while FIG. 2 suggests that the signals received by the receiver 64 are received after being reflected from the moving middle ear component 26, it is to be understood that signals that pass through the middle ear may also be affected in some detectable way by movement of the middle ear component 26. Thus, it is to be understood that the receiver 64 may be physically located anywhere within or without the middle ear so long as it is able to receive signals affected by the motion of the middle ear component 26.

Figure 3:
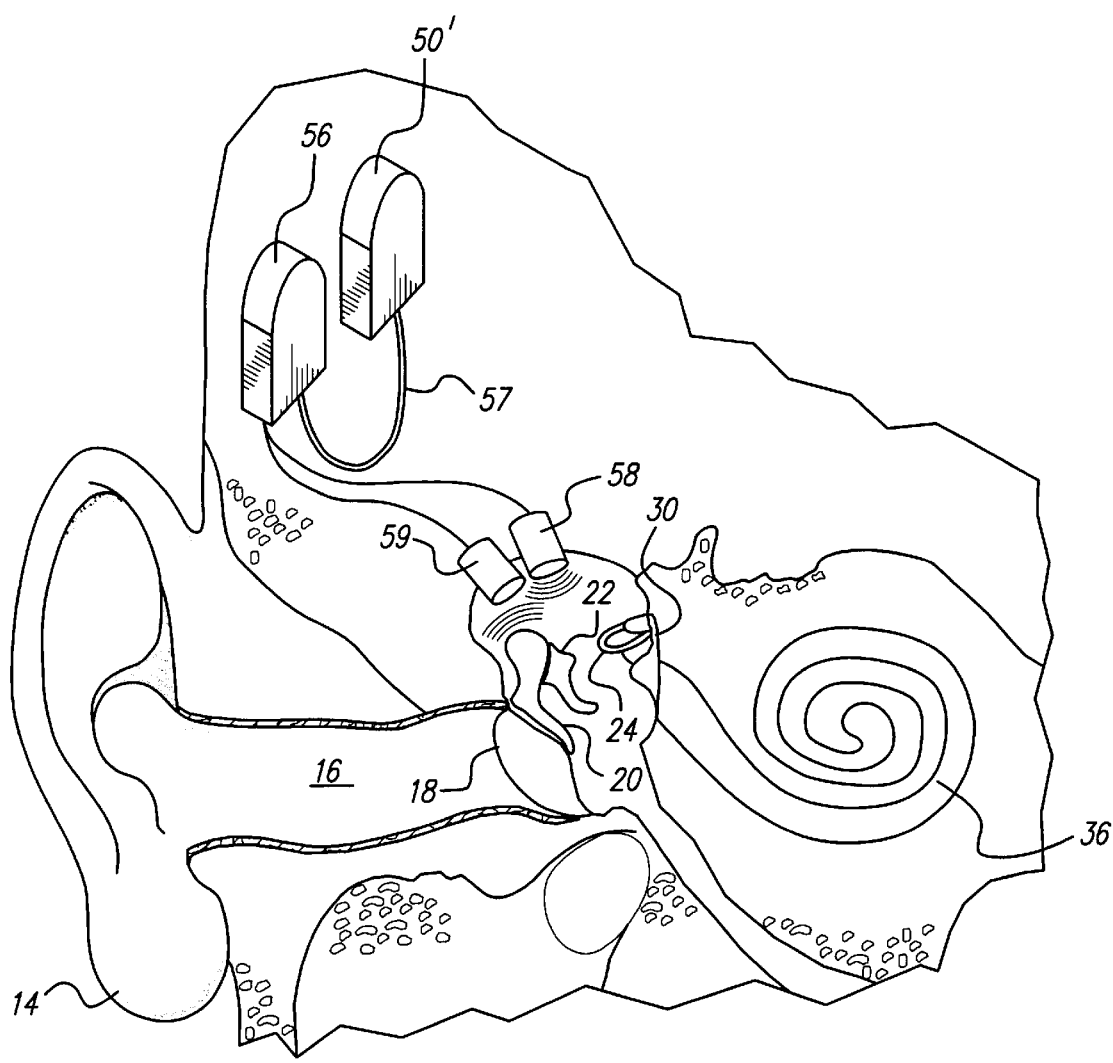
FIG. 3 shows one embodiment of the invention that includes the use of dual transducers operating in a continuous wave (CW) Doppler mode.

One implementation of a microphone system 10 using ultrasonic Doppler shift is illustrated in FIG. 3. The embodiment of the invention shown in FIG. 3 includes the use of dual transducers 58 and 59 operating in a continuous wave (CW) Doppler mode. As seen in FIG. 3, an implanted ICS 50' is coupled to an implantable speech processor and power module 56 via a suitable connecting cable 57. Dual acoustic piezoelectric CW Doppler transducers 58 and 59 are coupled to the implanted speech processor and power module 56. The transmit (TR) Doppler transducer 58 interrogates one of the moving elements of the middle ear, e.g., the malleus 20. The echo is reflected back and detected by the receiving (REC) transducer 59. The received echo signal is then amplified and demodulated to yield a signal, the output signal 67, that can be used to represent the motion of the tympanic membrane 18.

In FIG. 3, the transmitting acoustic transducer 58 and the receiving acoustic transducer 59 are both placed in a position to interrogate the head of the malleus 20, although; any other moving target would be as effective. The transmitting transducer continuously exposes the target to a sine wave signal $f_0$. This signal is scattered with some of the energy reflected back to the receiving transducer. If the malleus 20 is moving, this reflected signal is modulated by the Doppler effect so the received signal $f_r=f_0 \pm f_m$, where $f_m$ is the Doppler modulation frequency. This signal is then amplified and processed into a usable speech signal by the electronics and software located in the system speech processor (which function as the control circuit 66 shown in FIG. 2).

Figure 4:
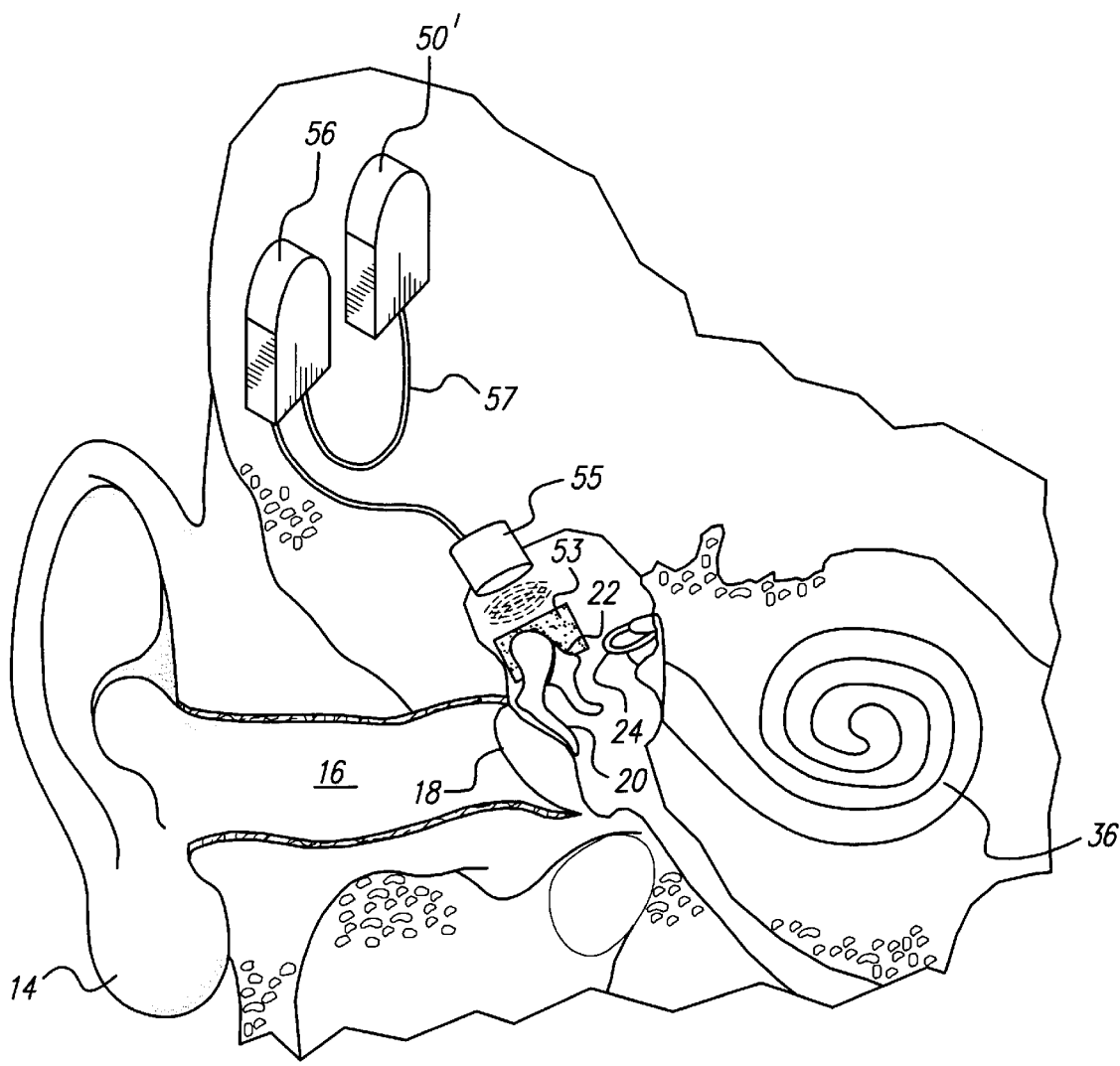
FIG. 4 illustrates another embodiment of the invention that uses a split piezoelectric transducer.

Dual-D CW Doppler transducers are available that provide both receiving and transmitting functions in a single package, and such may also be used to implement the microphone system of the present invention, as illustrated in FIG. 4. These devices have been used in diagnostic ultrasound systems for several years and have the advantage that the transducers can be matched in phase and amplitude for improved Doppler performance. As seen in FIG. 4, a split-D piezoelectric acoustic CW Doppler transducer 55 is used as both a transmitter and a receiver. In operation, one half of the Doppler transducer 55 interrogates the moving elements of the middle ear while the other half receives the reflected signal. The reflected signal is processed to extract the motion signal and convert it into an acoustic microphone signal. If desired, a reflector element 53 may be added to the malleus 20 in order to enhance (e.g., increase the amplitude of) the reflected signal.

Figure 5:
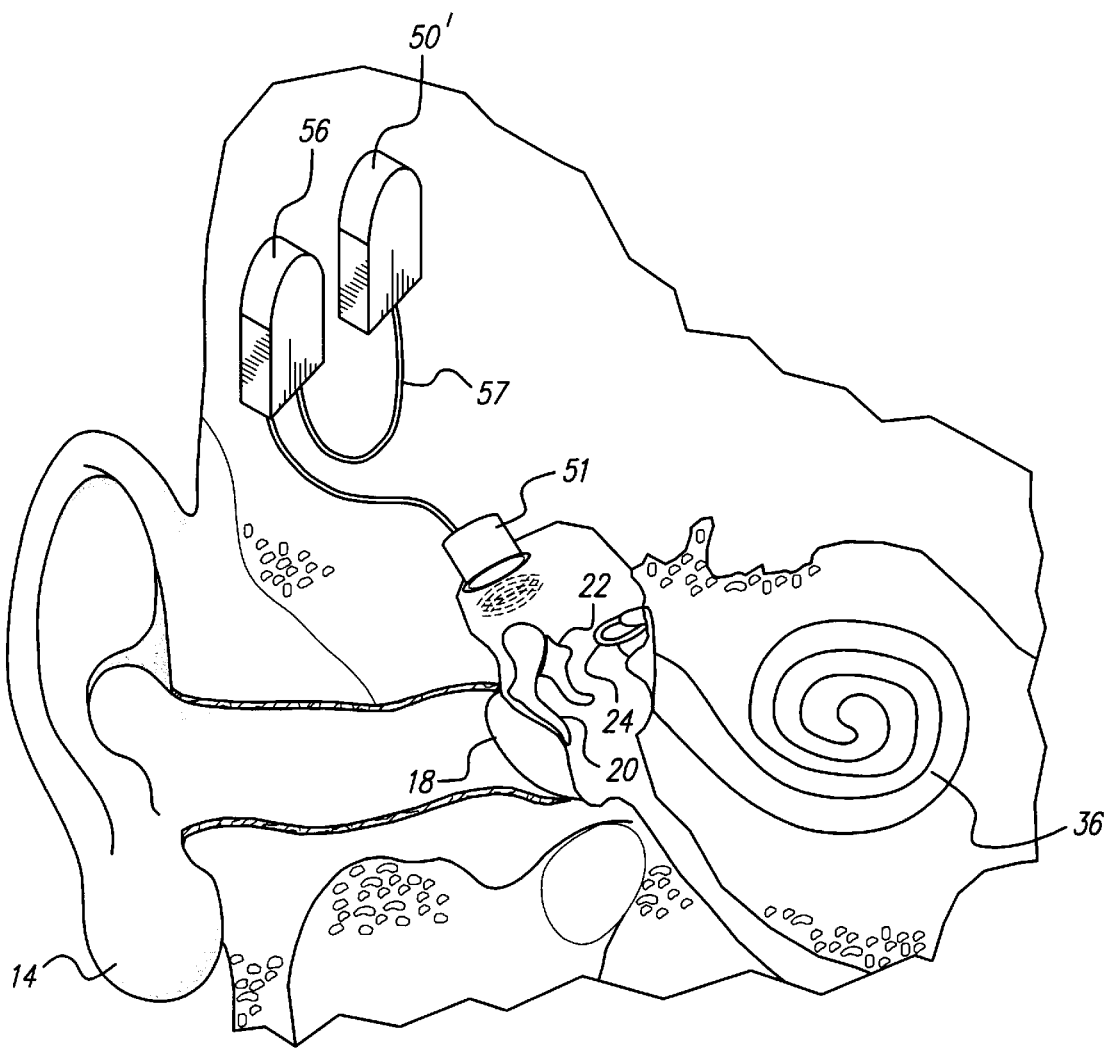
FIG. 5 depicts yet another embodiment of the invention utilizing a single transducer operating in a pulsed echo burst Doppler mode.

A lower power version of the invention, effective for low frequency speech signals, is illustrated in FIG. 5. In FIG. 5, the Doppler shift signal is obtained using a pulse/echo method employing a single Doppler transducer 51. In FIG. 5, a sine wave burst signal is transmitted towards the target, e.g., the malleus 20, for a short period of time (transmit burst time T1). The transmitter is then turned off and the same transducer 51 acts as a receiver for a "listen" time T2 (where T2 immediately follows T1), during which listen time the transducer 51 detects the reflected signal. Once received, the signal is amplified to derive the Doppler shift. This signal can then be used to represent the acoustic response, i.e., the output signal 67 (FIG. 2), of the microphone system 10 made in accordance with the invention using existing components of the user's ear. Care should be exercised, as required, with the pulse repetition frequency of the transmitter in order to avoid under sampling problems. A reflector may be added to the moving middle ear component, as illustrated, e.g., in FIG. 4, to increase the intensity of the reflected signal.

Figure 6:
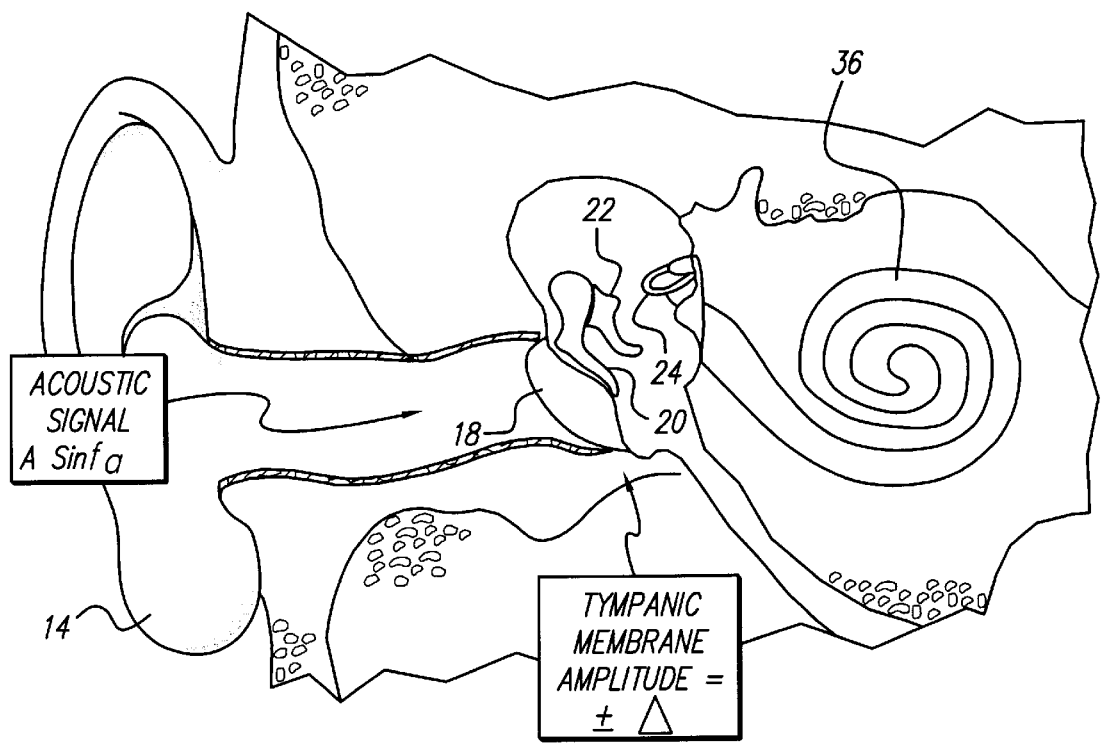
FIG. 6 illustrates the derivation of the Doppler shift equation for use with the invention.

FIG. 6 depicts the Doppler Shift equations that may be used with the invention. The amount of the Doppler shift resulting from a moving object is determined by the wavelength of the interrogating signal and the displacement amplitude of the object. For example, an acoustic signal 12 may be represented by the expression $A*\sin f_a$, where A is the amplitude of the signal, and $f_a$ is the frequency of the acoustic signal 12, and the sine function is used to model the varying nature of the acoustic signal 12. When the incoming signal 12 impinges upon or strikes the tympanic membrane 18, the tympanic membrane displaces or moves an amount $\pm\Delta$, where $\Delta$ is the amplitude of the displacement. The mean velocity V of the tympanic membrane, or other target object, may be expressed as $V=f_a \cdot (\pm\Delta)$. If c is the velocity of sound, which may be, e.g., approximately 300 m/sec in air, or 1540 m/sec in water, and if the Doppler interrogation frequency is $f_0$ (i.e., the frequency of the signal generated by the transmitter portion 62 within the sensor 60, see FIG. 2), then the Doppler shift frequency, $\Delta F$, may be expressed as:

$$\Delta F = 2Vf_0/c.$$

As described above, it is thus seen that the present invention provides an implantable microphone that may be used with a cochlear implant or other hearing aid system. More particularly, it is seen that the invention provides an implantable microphone system that advantageously utilizes many of the natural acoustic properties of the ear, such as its ability to use the outer ear to collect and direct sound into the ear canal, and its functioning middle ear components, to generate an electrical output signal 67 (see FIG. 2) of the microphone system that is representative of the sensed sound.

While the invention herein disclosed has been described by means of specific embodiments and applications thereof, numerous modifications and variations could be made thereto by those skilled in the art without departing from the scope of the invention set forth in the claims.

What is claimed is:

1. An implantable microphone system comprising:
    a sensor for sensing motion of middle ear components without physical contact with middle ear components, the sensor being at least partially implantable within the middle ear;
    processing means coupled to the sensor for converting the sensed motion to an electrical signal, the electrical signal comprising a microphone output signal that varies as a function of acoustic sound waves received through the outer ear and impressed upon the movable middle ear components.

2. The implantable microphone system of claim 1 wherein the sensor comprises first and second piezoelectric Doppler sensors, the first sensor having means for transmitting an interrogation signal towards at least one of the moving components of the middle ear, and the second sensor having means for sensing a reflected echo signal; and wherein the processing means includes means for amplifying and demodulating the reflected echo signal and producing the microphone output signal therefrom.

3. The implantable microphone system of claim 2 wherein the first and second piezoelectric Doppler sensors operate in a continuous wave (CW) mode.

4. The implantable microphone system of claim 1 wherein the sensor comprises a split piezoelectric Doppler transducer having first and second halves, a first transducer half having means for transmitting an interrogation signal towards at least one of the moving components of the middle ear, and a second transducer half having means for sensing a reflected echo signal; and wherein the processing means includes means for amplifying and demodulating the reflected echo signal and producing the microphone output signal therefrom.

5. The implantable microphone system of claim 4 wherein the split piezoelectric Doppler Transducer operates in a continuous wave (CW) mode.

6. The implantable microphone system of claim 1 wherein the sensor comprises a pulsed Doppler transducer that interrogates at least one of the moving elements of the middle ear for a short time period with a transmitted narrow band burst of signal energy, and then listens for reflected energy after the short time period, and wherein the processing means includes means for removing a shift in frequency of the reflected energy caused by a Doppler shift, and producing the microphone output signal as a function thereof.

7. An implantable microphone system comprising:
- a signal emitter implantable in or near the middle ear that generates and emits a detectable signal having known characteristics;
- wherein the detectable signal irradiates and is modulated by moving components of a user's middle ear when the signal emitter is implanted in or near the middle ear;
- a signal receiver that receives the detectable signal after modulation by moving components of the user's middle ear;
- wherein neither the signal emitter nor signal receiver are in physical contact with moving components of the user's middle ear; and
- signal demodulation means for demodulating signals received by the signal receiver means and creating therefrom a microphone signal having variations therein that vary as a function of the movement of middle ear components.

8. The implantable microphone system of claim 7 wherein the signal emitter comprises an optical emitter that emits an optical signal.

9. The implantable microphone system of claim 7 wherein the signal emitter comprises an infrared emitter that emits an infrared signal.

10. The implantable microphone system of claim 7 wherein the signal emitter comprises a radio frequency (RF) emitter that emits an RF signal.

11. The implantable microphone system of claim 7 wherein the signal emitter comprises an ultrasonic emitter that emits a pulsed ultrasonic signal.

12. The implantable microphone system of claim 11 wherein the signal demodulation means comprises an ultrasonic detector that receives acoustic reflections from the moving middle ear components when such components are irradiated by the pulsed ultrasonic signal generated by the ultrasonic emitter, and wherein the received signal shifts up or down in frequency by an amount proportional to the velocity and displacement of the middle ear moving components.

13. A method of sensing sound using implantable components and generating a microphone signal representative of the sensed sound, wherein the microphone signal is useable by a hearing aid device, including a cochlear implant system, the method comprising:
- (a) implanting a motion sensor in the middle ear, the motion sensor including means for sensing movement of at least one middle ear component without physically touching the at least one middle ear component;
- (b) sensing motion of at least one of the moveable middle ear components using the implanted motion sensor; and
- (c) converting the sensed motion of at least one middle ear component to the microphone signal representative of sensed sound.

14. The method of claim 13 wherein step (b) comprises sensing motion by transmitting from the motion sensor an incident signal that is directed to the at least one moveable middle ear component, and sensing a Doppler shift in frequency of a reflected echo signal from the at least one middle ear component, which reflected echo signal results from application of the incident signal.

15. The method of claim 13 wherein step (b) comprises sensing motion by transmitting from the motion sensor an incident optical signal that is directed to the at least one moveable middle ear component, and sensing variations in magnitude of the optical signal after the optical signal has passed through the middle ear and been modulated by movement of the at least one middle ear component.

16. The method of claim 13 wherein step (b) comprises sensing motion by transmitting from the motion sensor an incident optical signal that is directed to the at least one moveable middle ear component, and sensing variations in magnitude of the optical signal after the optical signal has reflected from and been modulated by movement of the at least one middle ear component.

17. The method of claim 13 wherein step (b) comprises sensing motion by transmitting from the motion sensor an incident infrared signal that is directed to the at least one moveable middle ear component, and sensing variations in magnitude of the infrared signal after the infrared signal has been affected by movement of the at least one middle ear component.

18. The method of claim 13 wherein step (b) comprises sensing motion by transmitting from the motion sensor an incident RF signal that is directed to the at least one moveable middle ear component, and sensing variations in magnitude of the RF signal after the RF signal has been affected by movement of the at least one middle ear component.

* * * * *